United States Patent
D'Angelo et al.

(10) Patent No.: US 10,926,351 B2
(45) Date of Patent: Feb. 23, 2021

(54) METHOD FOR PERFORMING A NOISE REMOVAL OPERATION ON A SIGNAL ACQUIRED BY A SENSOR AND SYSTEM THEREFROM

(71) Applicant: C.R.F. Società Consortile per Azioni, Orbassano (IT)

(72) Inventors: Giuseppe D'Angelo, Orbassano (IT); Gianmarco Genchi, Orbassano (IT); Alessandro Cisi, Orbassano (IT); Giorgio Pasquettaz, Orbassano (IT)

(73) Assignee: C.R.F. SOCIETA CONSORTILE PER AZIONI, Orbassano (IT)

(*) Notice: Subject to any disclaimer, the term of this patent is extended or adjusted under 35 U.S.C. 154(b) by 461 days.

(21) Appl. No.: 16/008,840

(22) Filed: Jun. 14, 2018

(65) Prior Publication Data
US 2019/0022791 A1     Jan. 24, 2019

(30) Foreign Application Priority Data
Jun. 19, 2017 (EP) ..................................... 17176639

(51) Int. Cl.
*G01N 33/48*     (2006.01)
*B23K 26/03*     (2006.01)
(Continued)

(52) U.S. Cl.
CPC .......... *B23K 26/032* (2013.01); *A61B 5/0402* (2013.01); *A61B 5/0488* (2013.01);
(Continued)

(58) Field of Classification Search
CPC .......... G06F 19/18; G06F 19/24; G06F 19/20; G06F 19/22; G06F 19/16
(Continued)

(56) References Cited

U.S. PATENT DOCUMENTS

| | | | | |
|---|---|---|---|---|
| 5,379,352 A | * | 1/1995 | Sirat ....................... | G06F 17/16 382/276 |
| 5,583,951 A | * | 12/1996 | Sirat ....................... | G06F 17/16 382/232 |
| 2012/0051475 A1 | * | 3/2012 | Hombs .............. | H03H 21/0012 375/350 |

FOREIGN PATENT DOCUMENTS

| | | |
|---|---|---|
| EP | 1275464 A1 | 6/2002 |
| EP | 1767308 A1 | 3/2007 |
| EP | 2624091 A1 | 8/2013 |

OTHER PUBLICATIONS

R. Vautard et al. "Singular Spectrum Analysis: A toolkit for short, noisy chaotic signals" Physica D, North-Holland, Amsterdam, NL, vol. 58, No. 1-4 Sep. 15, 1992.

(Continued)

*Primary Examiner* — Md M Rahman
(74) *Attorney, Agent, or Firm* — Heslin Rothenberg Farley & Mesiti P.C.; Victor A. Cardona, Esq.

(57) ABSTRACT

A method for performing a noise removal operation includes decomposing an acquired signal considered as one dimensional series. A trajectory matrix is constructed, transforming the trajectory matrix in a form to which single value decomposition is applicable. A single value decomposition is done on the transformed matrix computing eigenvalues and eigenvectors of the matrix. A one dimensional series is reconstructed, corresponding to the denoised signal. After the single value decomposition operation is provided, a single value decomposition is applied sequentially starting from a given window value. For each iteration, the root mean square value is calculated between a current and previous eigenvalue, calculating a minimum and its position of said root mean square value. The iterations are halted if the minimum is lower than a determined threshold value, (Continued)

otherwise increasing the window value and returning to the operation of decomposition of the acquired signal.

20 Claims, 8 Drawing Sheets

(51) Int. Cl.
  *G05B 19/418*  (2006.01)
  *G06T 5/00*  (2006.01)
  *A61B 5/0402*  (2006.01)
  *A61B 5/0488*  (2006.01)
  *A61B 5/00*  (2006.01)
  *B23K 31/12*  (2006.01)
  *G01J 3/28*  (2006.01)
  *G01N 21/27*  (2006.01)
  *G01N 21/88*  (2006.01)
  *G06F 17/16*  (2006.01)

(52) U.S. Cl.
  CPC .......... *A61B 5/7203* (2013.01); *B23K 26/034* (2013.01); *B23K 31/125* (2013.01); *G01J 3/2803* (2013.01); *G01N 21/274* (2013.01); *G01N 21/8851* (2013.01); *G05B 19/418* (2013.01); *G06F 17/16* (2013.01); *G06T 5/002* (2013.01); *G06T 2207/30048* (2013.01); *G06T 2207/30152* (2013.01)

(58) Field of Classification Search
  USPC .......................................................... 702/19
  See application file for complete search history.

(56) References Cited

OTHER PUBLICATIONS

Jie Ma et al. "Application of Singular Spectrum Analysis to the Noise Reduction of Intrusion Detection Alarms", Journal of Computers, vol. 6, No. 8. Aug. 1, 2011.

N.E. Huang, Z. Shen et al. "The empirical mode decomposition and the Hilbert spectrum for nonlinear and non-stationary time series analysis", Proceedings of the Royal Society of London. Series A: Methematical, Physical and Engineering Sciences, vol. 454, No. 1971 1988.

G. D'Angelo. "Advanced Signal Analysis Method to Evaluate the Laser Welding Quality", AKL—International Laser Technology Congress May 9, 2012.

Extended European Search Report dated Oct. 11, 2017, completed on Sep. 29, 2017 for corresponding EP application No. 17176639.7-1906.

\* cited by examiner

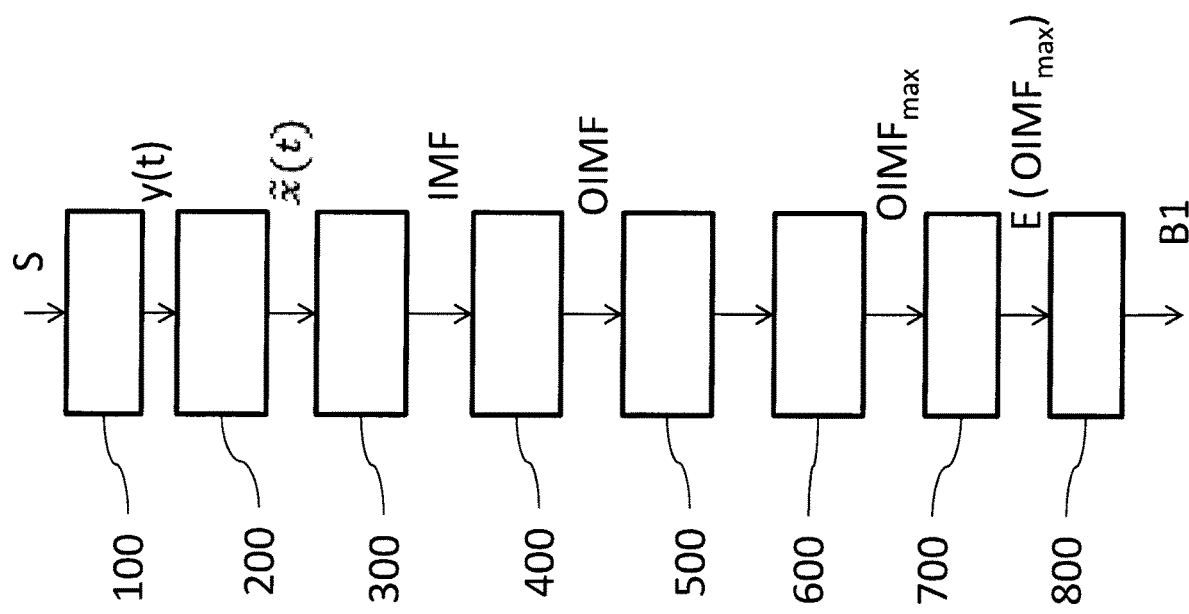

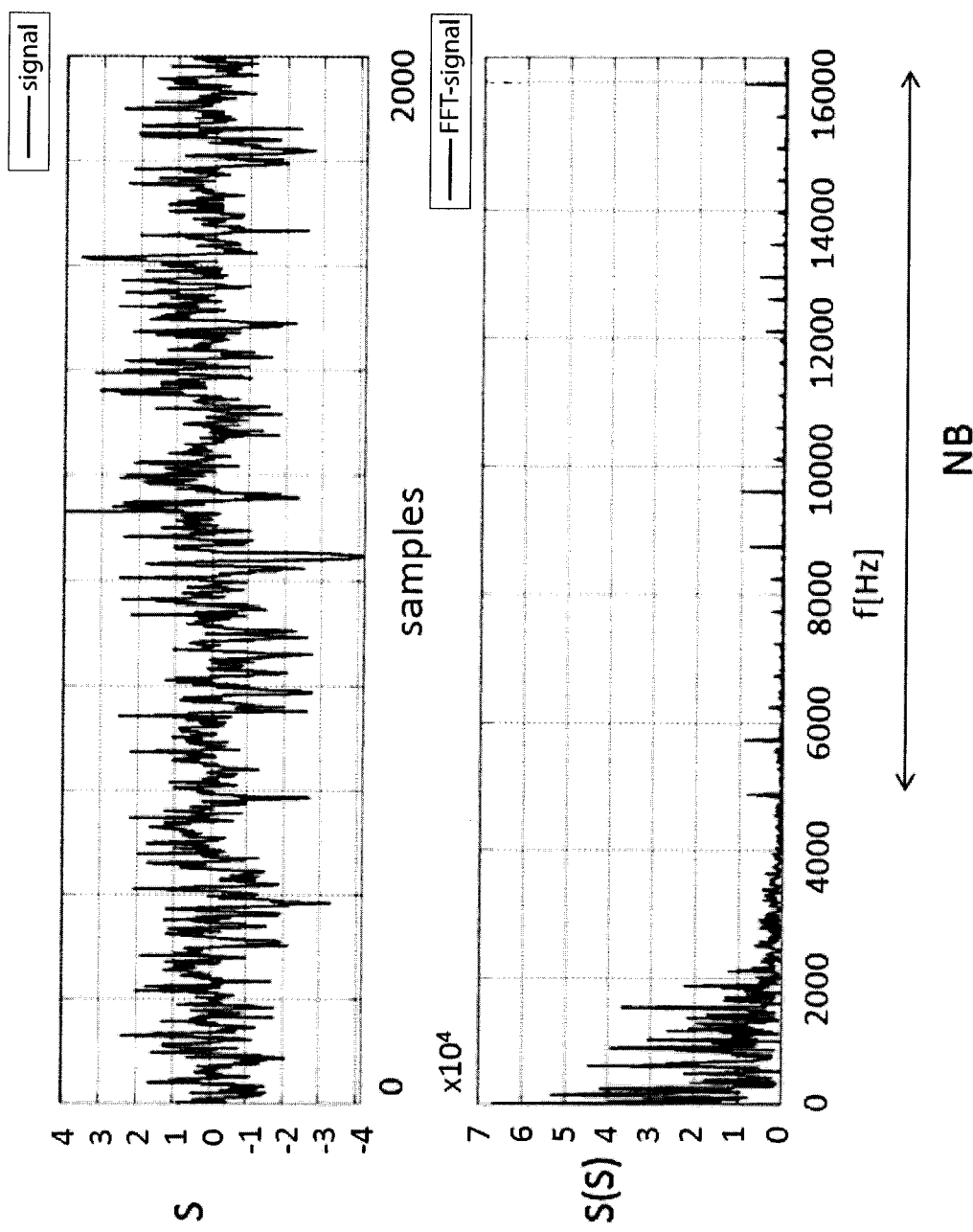

METHOD FOR PERFORMING A NOISE REMOVAL OPERATION ON A SIGNAL ACQUIRED BY A SENSOR AND SYSTEM THEREFROM

CROSS-REFERENCE TO RELATED APPLICATIONS

This application claims priority to European Patent Application No. 17176639.7 filed on Jun. 19, 2017, the entire disclosure of which is incorporated herein by reference.

FIELD OF THE INVENTION

The present invention relates to methods for performing a noise removal operation on a signal acquired by a sensor obtaining a denoised signal, said noise removal operation including a Singular Spectrum Analysis (SSA).

The solution refers in particular to signal acquired by a sensor operating in a industrial process, like laser welding or laser cutting.

Laser welding is increasingly used in industrial applications, because of the advantages it offers, such as high speed, high accuracy, low heat input and low distortion. As for any other fusion welding process, weld imperfections can occur. Because of the small features of a laser weld and thereby of the imperfections that may occur, the industrial requirement is to detect these reliably using real-time monitoring methods. In the automotive industry the demand for real-time monitoring methods has become increasingly urgent since for reducing vehicle weight and improve fuel efficiency and safety, the development of lightweight and high-strength vehicles has prompted an increased use of advanced high strength steels (AHSS). Additionally, these steels are galvanized in order to improve the surface corrosion resistance for automotive parts. However, it is still a great challenge performing the laser weld of galvanized steels in a zero-gap lap joint configuration. When laser welding of galvanized steels in a zero-gap lap-joint configuration, the zinc coating at the contact interface will vaporize; due to the lower boiling point (906° C.) of zinc as compared to the melting Monitoring must be fast, reliable and cost-effective, as components with defects either have to be rectified or scrapped, both having a considerable impact on the cost of the component. Most common techniques in use today for process monitoring, employ photodiode sensors to record electromagnetic signals arising from the molten pool during welding, with the objective of correlating the output from the sensor to features such as weld penetration, the occurrence of pin holes, or weld shape. These systems have been developed to monitor laser welding in real-time and generally examine the laser-to-metal interactions to infer the quality of the weld itself. By using different types of sensors, responding to different wavelengths of light, different aspects of the process or weld can be monitored, such as the weld pool temperature, the plasma above the weld pool and the level of back reflection, for instance. Different detectable emissions can be used as the process signals: a) the reflected laser, originated from the amount of the laser source radiation which is not absorbed by the material, b) acoustic emissions, originated from the stress waves induced by changes in the internal structure of a work piece, c) radiation emitted from the metal vapour and the molten pool. By using the optical emissions, it is possible to evaluate laser process quality, in particular, to find out the relationship between emission characteristics and weld quality characteristics. Since these techniques are indirect, they require accurate signal interpretation and processing to infer information about the actual condition of the weld: the more accurate signal analysis technique, the better weld quality characterization.

In the following it is in particular discussed the the condition monitoring of a laser welding process under varying operating conditions, which cause non-stationary. To deal with nonstationary signals, attention has been given to time-frequency analysis methods such as the Wigner-Ville distribution, wavelet analysis, cyclo-stationary analysis and spectral correlation. Wavelet analysis is probably the most popular technique, but has the drawback that the basis functions of the decompositions are fixed and do not necessarily match the varying nature of the signals.

Relatively recently, in the quest for accurate time and frequency resolution, in N. E. Huang, Z. Shen et al: 'The empirical mode decomposition and the Hilbert spectrum for nonlinear and non-stationary time series analysis', Proceedings of the Royal Society of London. Series A: Mathematical, Physical and Engineering Sciences, Vol. 454, No. 1971, (1998), pp. 903-995 is proposed the Empirical Mode Decomposition method (EMD). The EMD technique decomposes the signal into intrinsic mode functions and the instantaneous frequency and amplitude of each intrinsic mode function can be then obtained, most commonly by applying the Hilbert Transform. An alternative approach in order to obtain the instantaneous characteristics of the decomposed signals, is to use an energy tracking operator to estimate the energy of the signal, as developed by Teager and introduced by Kaiser, F. Kaiser, 'On Teager's energy algorithm and its generalization to continuous signals', Proceedings of IEEE DSP Workshop, (1990) and then use an energy separation algorithm for the estimation of the amplitude envelope and instantaneous frequency of each intrinsic mode function (IMF) produced by the EMD method. The above mentioned method promises high resolution and low computational power compared to other widely used time-frequency techniques. All IMFs should reconstruct the original data set and they should be orthogonal to each other. The empirical mode decomposition (EMD) method proposed by Huang however does not guarantee the orthogonality of IMFs. The imperfect orthogonality among the IMFs introduces a severe energy leakage.

To overcome this problem, a new method based on the Gram-Schmidt orthogonalization method referred as the orthogonal empirical mode decomposition (OEMD) has been proposed by the inventor, for instance in the publication G. D'Angelo: 'Advanced Signal Analysis Method to Evaluate the Laser Welding Quality', AKL—International Laser Technology Congress, May 9-11, 2012 in Aachen to improve the degree of orthogonality among the IMFs and attain the complete orthogonal intrinsic mode functions (OIMFs). The above mentioned method promises high resolution and low computational power compared to other widely used time-frequency techniques.

However, the optical signals detected during the laser welding are typically contaminated by different kind of noises that affect the photo-detector or pyrometer used. To avoid this phenomenon, it is necessary to smooth and de-noise the signal for getting a "clean" signal. Although several methods have been developed to reduce the effect of noise, one of the most effective methods of dealing with noise contamination is to filter the noise out of the signal while retaining as much as possible of the region of interest in the frequency spectrum. The traditional method to de-noise process signals is to use digital Butterworth filters. Nonetheless, more advanced filtering techniques such as discrete wavelet transforms, Wiener filtering have also been used to that end. Although these methods have proven useful, their main drawback is the complexity of devising an automatic and systematic procedure, i.e., a mother wavelet function must be selected when using discrete wavelet transforms, the filtering function parameters must be chosen when using the Wiener filter, etc.

Object of the Invention

The object of the present invention is to overcome all the aforesaid drawbacks of the noise removal operation, in particular in connection with monitoring of industrial work processes.

In view of achieving said object, the invention relates to a method for performing a noise removal operation on a signal acquired by a sensor having the characteristics set out in the foregoing and further characterized by the fact that said noise removal operation includes modified Singular Spectrum Analysis (SSA) including performing iteratively an operation of decomposition of said acquired signal considered as one dimensional series, an operation of construction of a trajectory matrix, transforming said trajectory matrix in a form to which single value decomposition is applicable, an operation of single value decomposition on said transformed matrix computing eigenvalues and eigenvectors of said matrix, an operation of reconstruction of a one dimensional series corresponding to said denoised signal based on selected among said eigenvalues, wherein after the single value decomposition operation is provided applying sequentially a single value decomposition starting from a given window value, in particular a value of three, for each iteration, calculating the root mean square value between the current and previous eigenvalue, calculating a minimum and its position of said root mean square value halting the iterations if said minimum is lower than a determined threshold value, in particular lower than 1, otherwise increasing the window value and returning to the operation of decomposition of said acquired signal.

In the preferred embodiment, a method for monitoring the quality of an industrial working process, which includes identifying defects of the working process, of the type comprising the steps of:

acquiring a signal having multiple frequency components from the industrial working process, performing a noise removal operation on said acquired signal obtaining a denoised signal, decomposing said denoised signal in signals having single frequency components and performing a subsequent orthogonalization to obtain orthogonalized components having a single frequency component, calculating for each intrinsic orthogonalized component the respective energy, selecting the intrinsic orthogonalized component with the highest energy value, estimating the instantaneous energy of the intrinsic orthogonalized component with the highest energy value applying a energy tracking operator, performing a procedure of defect identification on the instantaneous energy of the intrinsic orthogonalized component with the highest energy value, wherein the noise removal operation is performed according to the above indicated method for performing a noise removal operation on a signal acquired by a sensor.

The invention also relates to a system for monitoring the quality of industrial processes which implements the method for monitoring the quality of industrial processes described above, as well as the corresponding computer product directly loadable into the memory of a digital computer such as a processor and comprising software code portions to perform the method according to the invention when the product is run on a computer.

BRIEF DESCRIPTION OF THE DRAWINGS

Additional characteristics and advantages of the present invention shall become readily apparent from the description that follows with reference to the accompanying drawings, provided purely by way of explanatory and non limiting example, in which:

FIG. 2 shows a basic flow diagram of a monitoring method implementing the method according to the invention;

FIG. 5A is a diagram of amplitude versus sample displaying a signal process by the method of FIG. 2;

FIG. 5B is a diagram of amplitude versus frequency displaying a signal processed by the method of FIG. 2;

DETAILED DESCRIPTION OF THE INVENTION

Figure 1:
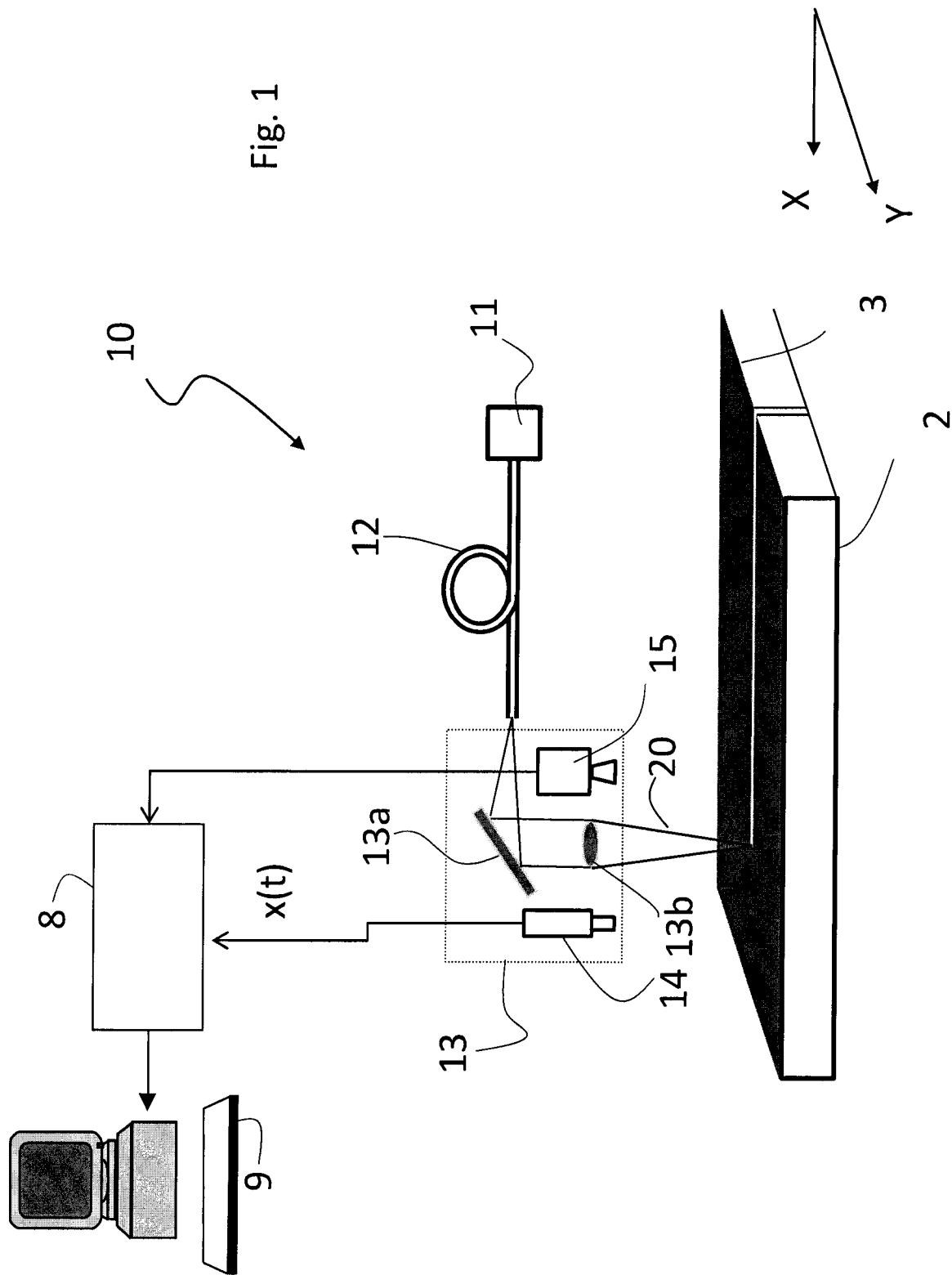
FIG. 1 is a block diagram showing a system that implements the method according to the invention.

With reference to FIG. 1, the reference number 10 designates a system for monitoring the quality of a laser welding process. The example refers to the case of two metal work pieces 2, 3 which are welded together by means of a laser beam 20. The number 11 designates a laser source represented by a laser diode, coupled via a optic fiber 12 to a welding optic 13. In particular this is obtained by the head of a fiber coupled diode laser, which laser beam 20 is guided via an optical fiber 12 to the welding optic 13.

The welding optic 13 is schematically shown as including a mirror 13a, which can be also a beam splitter or semireflecting mirror beyond which sensors can be arranged to detect quantities from the welding process, such as radiation, and a focusing lens 13a whereat arrives the laser beam originated by the laser source represented by the laser diode 11.

The welding optic 13 is represented as including also a camera 15 and a photosensor 14. The camera 15 acquires an image of the welding spot while the photosensor 15 measures the electromagnetic of such welding spot through the emitted radiation. The output signals of the camera 14a and a photosensor 14b are sent to an acquisition board 8 which acquires and performs the necessary conversions on the signal and supply them to a personal computer 9 for analysis and processing.

It is here noted that the method according the invention preferably acquires a signal generated by the working process, i.e. a radiation emitted by the process as a result of the development of the working process, not a signal from the tool performing the process.

The signal acquired by the photosensor 14 during time is indicated in the following with S, and it is the signal having multiple frequency components acquired from the industrial working process, which will be discussed by way of example in the following to illustrate the method according to the invention.

With reference to the basic flow diagram of FIG. 2, the monitoring method envisages the following operation:

an operation 100 of acquisition of a sensor signal S. The sensor signal S is acquired at an acquisition frequency which in the embodiment here described is 32 KHz. In particular in the examples shown in FIGS. 5-10, data acquisition was performed with a NI Compact RIO multi-channel data acquisition board. Data sampling frequency=32768 Hz. In general the acquisition frequency is greater or equal than 32 Khz. The sensor signal S is originated for instance from a sensor such as the pyrometer 14 recording electromagnetic signals arising from the molten pool during welding. The acquisition operation 100 originates an acquired signal y(t) which is signal function of time an operation 200 of noise removal from the acquired signal y(t) originating a denoised signal x̃(t). The operation of noise removal 200 by a modified Single Spectrum analysis procedure which is detailed in FIG. 2;

an operation 300 on the denoised signal x(t) of decomposition in a plurality of monocomponent signals, indicated as Intrinsic Mode Functions $IMF_1 \ldots IMF_{n-1}$ using an Empirical Mode Decomposition procedure to decompose the denoised signal x̃(t) and get the Intrinsic Mode Functions $IMF_1 \ldots IMF_{n-1}$, a subsequent operation 400 of orthogonalization to obtain orthogonalized components $OIMF_1 \ldots OIMF_{n-1}$ having a single frequency component, an operation 500 of calculating for each intrinsic orthogonalized component $OIMF_1 \ldots OIMF_{n-1}$ the respective energy, an operation 600 of selecting the intrinsic orthogonalized component with the highest energy value ($OIFM_{max}$), an operation 700 f estimating the instantaneous energy E of the intrinsic orthogonalized component with the highest energy value $OIFM_{max}$ applying a energy tracking operator, such as Teager-Kaiser energy operators (TKEOS), an operation 800 of performing a procedure of defect identification on the instantaneous energy E of the intrinsic orthogonalized component with the highest energy value $OIFM_{max}$.

Therefore, more in detail, in the step 100 a sensor signal S is acquired.

In FIG. 5A is represented a diagram (amplitude vs. samples) displaying the signal S detected by photosensor 14 during the laser welding of overlapped HSS samples while FIG. 5B displays a relative spectrum S(S) (amplitude vs. frequency in Hz) where the noise spectral band NB is indicated.

The sensor signal S, with respect to the following noise removal operation 200 is considered as a real-valued non-zero time series of a sufficient length T, $Y_T=(y_1 \ldots y_T)$.

$$L\left(L \leq \frac{T}{2}\right),$$

is window length which is fixed, and let K=T−L+1.

Figure 3:
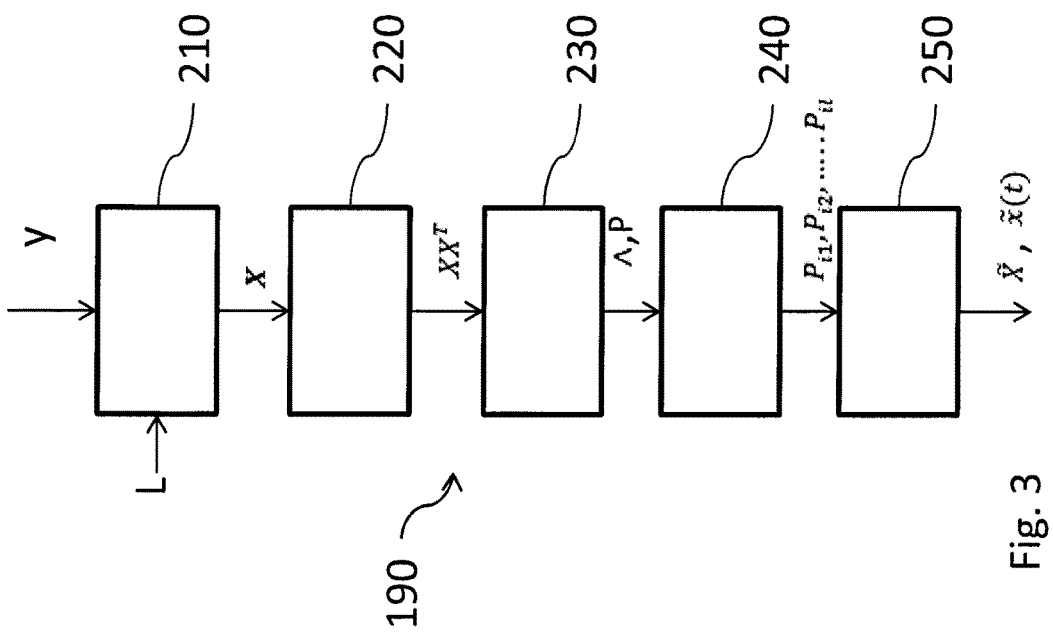
FIG. 3 is a flow diagram representing a noise removal method according to the prior art.

Now, in order to better understand the solution here described, it is described a conventional noise removal operation 190 of a Singular Spectrum Analysis (SSA), with reference to the diagram flow of FIG. 3.

There, with 210 is indicated a step of computing a trajectory matrix X. Such step 310 transfers the one-dimensional time series $Y_T=(y_1 \ldots y_T)$ into the multi-dimensional series $X_1 \ldots X_K$ with vectors $X_i=(y_i \ldots y_{i+L+1}) \in R^L$, where K=T−L+1.

The single parameter of the embedding is the window length L, an integer such that $2 \leq L \leq T$.

The result of this step is the trajectory matrix X $$X = (x_{ij})_{i,j=1}^{L,K} = \begin{pmatrix} y_1 & y_2 & \ldots & y_K \\ y_2 & y_3 & \ldots & y_{K+1} \\ \ldots & \ldots & \ldots & \ldots \\ y_L & y_{L+1} & \ldots & y_T \end{pmatrix}$$

The trajectory matrix X is a Hankel matrix, which means that all the elements along the diagonal i+j=const are equal.

With 220 is indicated a step of constructing a matrix $XX^T$ for applying the Single Value Decomposition, i.e the trajectory matrix X multiplicated by its transposed matrix $X^T$.

With 230 is indicated a step of performing a Single Value Decomposition of the matrix $XX^T$. In this step are computed the eigenvalues $\lambda_1, \lambda_2, \ldots \lambda_L$ and eigenvectors $P_1, P_2, \ldots P_L$ of the matrix $XX^T$ and represented in the form $XX^T=P\Lambda P^T$;

$\Lambda=diag(\lambda_1, \ldots, \lambda_L)$ is the diagonal matrix of eigenvalues of matrix $XX^T$ ordered so that $\lambda_1 \geq \lambda_2 \geq \ldots \lambda_L \geq 0$;

$P=(P_1, P_2, \ldots P_L)$ is the corresponding orthogonal matrix of eigen-vectors of matrix $XX^T$.

With 240 is indicated a subsequent step of selection of eigen-vectors. In this step is provided to select a group of l ($1 \leq l \leq L$) eigenvectors $P_{i1}, P_{i2}, \ldots P_{il}$. Such grouping step corresponds to splitting the elementary matrices $X_i$ into several groups and summing the matrices within each group. Let $I=(i_1, \ldots i_l)$ be a group of indices $\{i_1 \ldots i_l\}$. Then the elementary matrix $X_I$ corresponding to the group 1 is defined as $X_I=X_{i1}+ \ldots X_{il}$.

With 250 is then indicated a final step of reconstruction of the one-dimensional series. This includes computing a denoised matrix $$\tilde{X} = \|\tilde{x}_{ij}\| = \Sigma_{k=1}^{l} P_{ik} P_{ik}^{T} X$$

as an approximation to trajectory matrix X. Transition to a denoised one-dimensional series $Y_T = (y_1 \ldots y_T)$ is then achieved by averaging over the diagonals of the denoised matrix $\tilde{X}$, obtaining a denoised signal $\tilde{x}(t)$.

Figure 4:
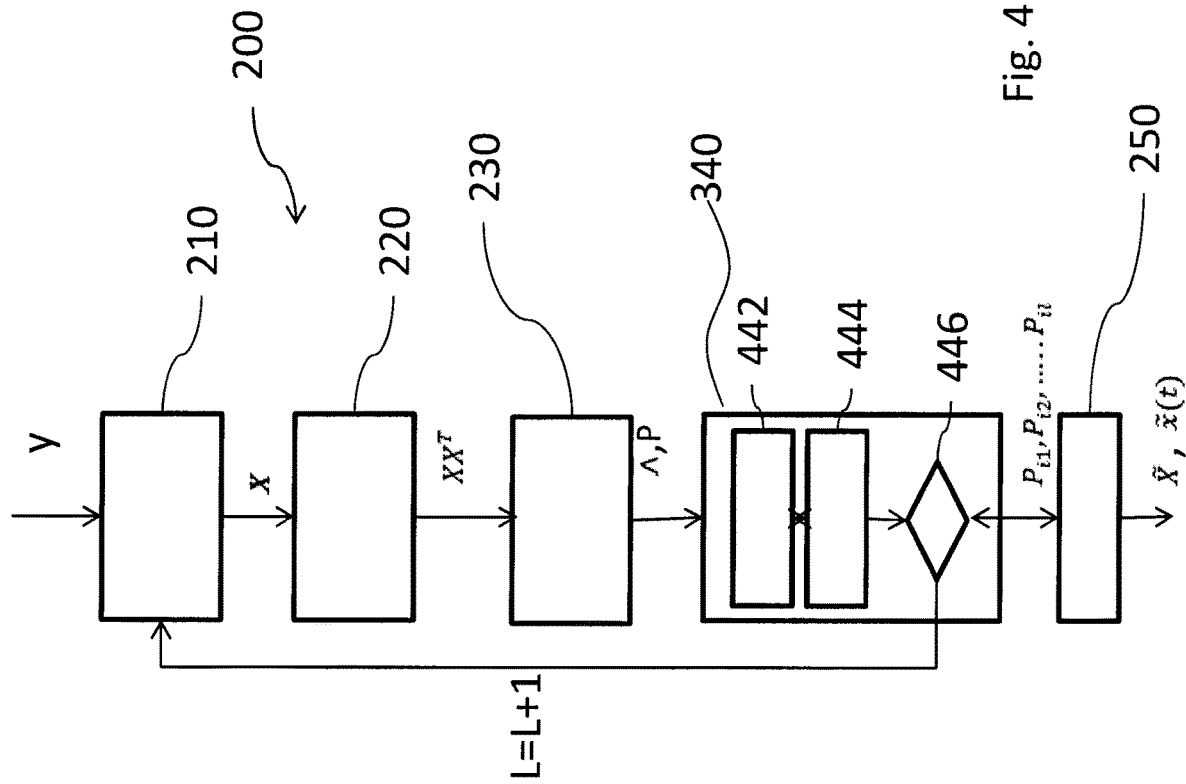
FIG. 4 is a flow diagram representing an embodiment of the noise removal method according to the invention.

One of the drawbacks of SSA ad described with reference to FIG. 3 is the lack of a general criterion to select the values of the parameters L (window length) and the grouping strategy used in the step 240. Moreover, certain choices of window lengths and grouping strategy lead to poor separation between trend and noise in the signal, i.e., trend components become mixed with noise components in the reconstruction of the signal. To overcome the uncertainty in what value of window length L to select, it is provided a modified SSA 200, described with reference to the flow diagram of FIG. 4.

As it can be seen, this is a iterative process where the grouping step 240 of FIG. 3 is substituted by a modified group selection step 340. Step 210, 220 and 230 correspond to those of FIG. 3, with the sole difference that the window length L values starts at value L=3 and it is increased at each iteration through the chain of step 210, 220, 230 commanded by the step 340. The reconstruction step 250 also is maintained.

Thus, the decomposition is carried out at step 230 starting from L=3, producing a corresponding number of eigenvalues $\lambda_1, \ldots, \lambda_L$ and eigenvector $P_1, P_2, \ldots P_L$, to step 340

Then, in a step 342 it is calculated the root mean square RMS between the current and previous eigenvalue of the set of eigenvalues.

$$RMS(1) = rms(\lambda_1 : \lambda_2)$$

...

$$RMS(L-1) = rms(\lambda_{L-1} : \lambda_L)$$

Then, in a step 344 it is calculated a minimum and its position min, posmin of the root mean square values for that iteration.

In step 346 is evaluated an halt criterion:

$$[min, pos_{min}] = min(RMS(RMS(1:L-1)) < \varepsilon = 1/100$$

Therefore in step 346 is provided halting the iterations if said minimum is lower than a determined threshold value ε in particular lower than 1, otherwise increasing the window value and returning to step 310 for a new iteration of the modified SSA operation 200.

The group of 1 (1≤l≤L) eigenvectors $P_{i1}, P_{i2}, \ldots P_{il}$ supplied to step 250 is selected with the value of L at which the iteration is stopped, for instance if L=5, is $P_{i1}, P_{i2}, \ldots P_{i5}$.

The convergence of this sequential procedure is such in that the percentage RMS difference between the current and previous signals in a given iteration is sufficiently small.

Figures 6A, 6B, 6C, 6D:
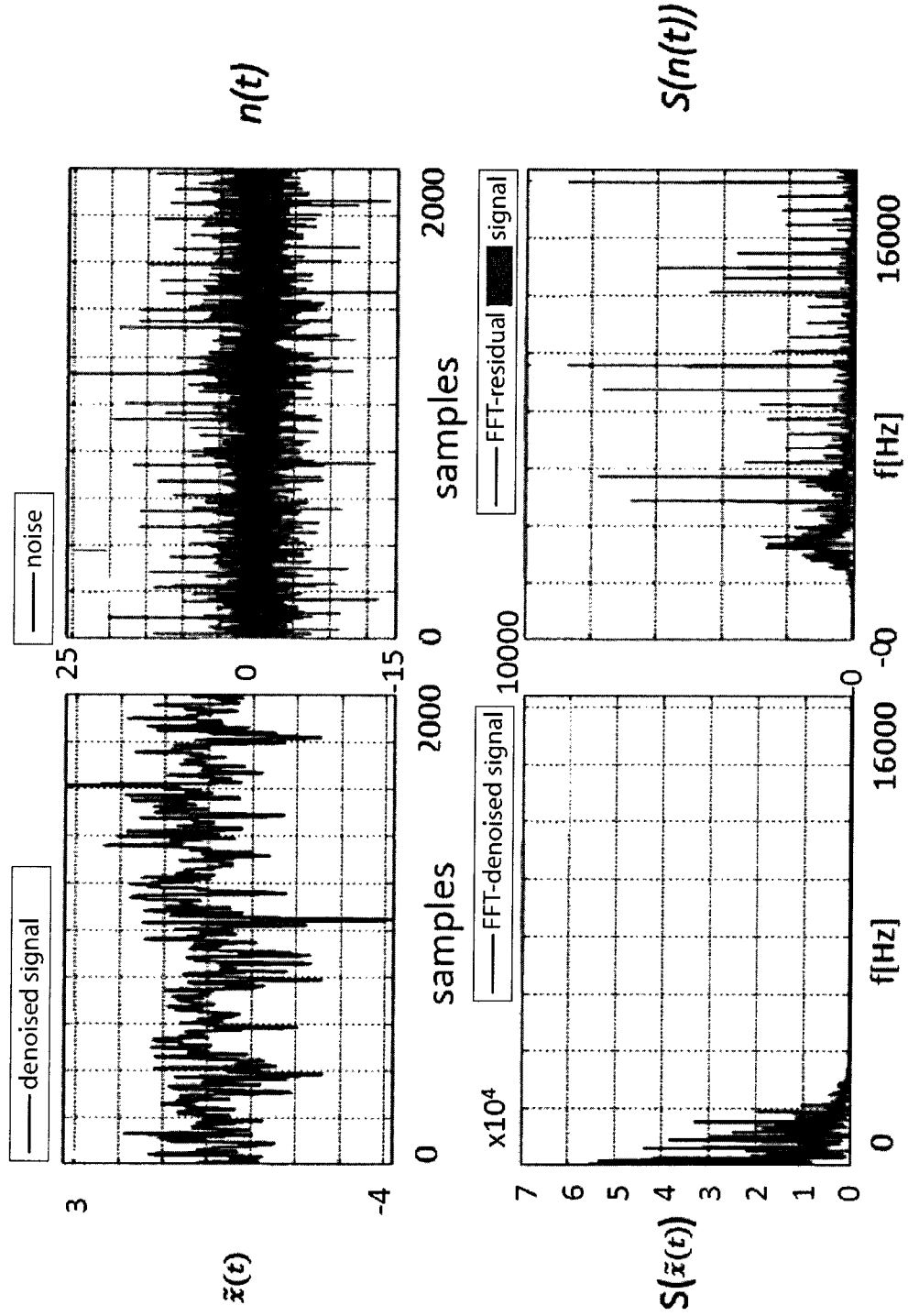
FIG. 6A is a diagram of a denoised signal processed by the method of FIG. 2.
FIG. 6B is a diagram of a relative spectrum of a signal processed according to the method of FIG. 2.
FIG. 6C is diagram of a residual noise of a signal processed according to the method of FIG. 2.
FIG. 6D is a diagram of a relative spectrum of a signal processed according to the method of FIG. 2.

FIG. 6A displays the denoised signal $\tilde{x}(t)$ and FIG. 6B the relative spectrum $S(\tilde{x}(t))$. FIG. 6C shows the residual noise n(t) and FIG. 6D shows its relative spectrum $S(n(t))$. The effectiveness of the proposed method of noise removal with modified SSA 200, for getting, in a blind way, the smoothed signal without fixing any initial conditions, has been demonstrated. It should be noted, looking at the spectra of FIG. 6B, denoised signal, and 6D, noise, the separation between the spectra. This condition ensures that the denoised signal is not contaminated by noise.

Now, to complete the description of the method for monitoring the quality of an industrial working process implementing the method for noise removal according to the invention, the remaining operations 300-800 are described.

The operation 300 is an operation of decomposition of the denoised signal $\tilde{x}(t)$, which in the following will be indicated as x(t) like a generic signal for simplicity, in a plurality of monocomponent signals, indicated as Intrinsic Mode Functions IMF1 . . . IMFn−1 using an Empirical Mode Decomposition procedure to decompose the signal x(t) and get the Intrinsic Mode Functions IMF1 . . . IMFn−1.

The Empirical Mode Decomposition method (EMD) is an empirical method used to decompose a multicomponent signal into a number of signal components (set of oscillatory functions) in the time-domain called intrinsic mode functions (IMF). Each IMF represents a bandwidth of frequencies of the signal, so the EMD method is a filter bank method, and can be used for removing unwanted components of the signal being analyzed. By definition, an IMF should satisfy the following conditions:

(a) the number of extrema and the number of zero crossings over the entire length of the IMF must be equal or differ at most by one, and (b) at any point, the mean value of the envelope defined by the local maxima and the envelope defined by the local minima is zero.

The EMD decomposition procedure for extracting an IMF is called the sifting process and consists of the following steps:

the local extrema and the local minima of the signal x(t) are found;

all the local extrema of the signal are connected to form an upper envelope u(t), and all the local minima of the envelope are connected to form a lower envelope l(t). This connection is made using a cubic spline interpolation scheme;

a mean value $m_1(t)$ is defined as:

$$m_1(t) = [l(t) + u(t)]/2$$

and a first possible component h1(t) is given by the equation:

$$h_1(t) = x(t) - m_1(t)$$

The component $h_1(t)$ is accepted as the first component only if it satisfies the conditions to be an IMF. If it is not an IMF, the sifting process is followed until $h_1(t)$ satisfies the conditions to be an IMF. During this process $h_1(t)$ is treated as the new data set, which means that its upper and lower envelopes are formed and the mean value of these envelopes, $m_{11}(t)$, is used to calculate a new component $h_{11}(t)$ hoping that it satisfies the IMF criteria:

$$h_{11}(t) = x(t) - m_{11}(t)$$

The sifting process is repeated until the component $h_{1k}(t)$ is accepted as an IMF of the signal x(t) and is denoted by $C_1(t)$:

$$C_1(t) = h_{1k}(t) = h_1(k-1)(t) - m_k(t)$$

The first IMF is subtracted from the signal x(t) resulting in the residual signal:

$$r_1(t) = x(t) C_1(t)$$

During the sifting process the signal x(t) is decomposed into a finite number N of intrinsic mode functions and as a result N residual signals are obtained. The process ends when the last residual signal, $r_N(t)$ is obtained and is a constant or a monotonic function. The original signal x(t) can be reconstructed as the sum:

$$x(t) = \sum_{j=1}^{N} C_j(t) + r_N$$

The nonstationary signal is decomposed into IMFs using the previously described EMD algorithm. Each IMF can be then analysed separately in order to obtain features for damage detection.

Then it is performed the subsequent operation of orthogonalization 400 to obtain orthogonalized components OIMF1 ... OIMFn−1 having a single frequency component, using in particular a method called Orthogonal Empirical Mode Decomposition (OEMD).

The EMD analysis is based on the hypotheses:
IMF got by EMD could re-compose original signal
there is orthogonality among IMF components.

The EMD approach proposed by Huang can't ensure strict orthogonality in theory, and only indicate approximately orthogonality among each IMF in numerical value. In order to check the orthogonality of IMFs from EMD, Huang et al. defined an overall index of orthogonality $IO_T$ and a partial index of orthogonality for any two components $IO_{jk}$, as follows:

$$IO_T = \sum_{j=1}^{n+1}\sum_{\substack{k=1\\k\neq j}}^{n+1} \int_0^T c_j(t)c_k(t)dt \bigg/ \int_0^T x^2(t)dt == \sum_{j=1}^{n+1}\sum_{\substack{k=1\\k\neq j}}^{n+1}\sum_{i=1}^{N} c_{ij}c_{ki} \bigg/ \sum_{i=1}^{N} x_i^2$$

$$IO_K = \int_0^T c_j(t)c_k(t)dt \bigg/ \int_0^T c_j^2(t)dt + \int_0^T c_k^2(t)dt = \sum_{j=1}^{N} c_{ji}c_{kl} \bigg/ \sum_{i=1}^{N} c_{ji}^2 + c_{kl}^2$$

In step 400 it is defined an energy index to indicate the orthogonality of IMF components. The energy of original signal $E_x$ and the energy of each IMF component are given by:

$$E_x = \int_0^T X^2(t)dt = \sum_{i=1}^{N} X_i^2$$

$$E_j = \int_0^T c_j^2(t)dt = \sum_{i=1}^{N} c_j^2 (j=1, \ldots, n+1)$$

If the IMF components from EMD are exactly orthogonal to each other, the value of orthogonality index $IO_T$ should be zeros, the total energy of decomposed signal $E_{tot}$ should be invariable and the energy leakage between any two IMF components $E_{jk}$ should be zero.

Generally, because the IMFs from EMD are not theoretically orthogonal, the value of orthogonality index is about from $10^{-2}$ to $10^{-3}$. Therefore, Huang considered that there is almost orthogonal among IMFs. However, numerical simulation demonstrated that owing to the minor error in orthogonality that Huang considered, there is actually severe energy leakage when applied EMD for the decomposition of time signals.

In order to ensure the exact orthogonality of IMFs from EMD and no energy leakage due to EMD, the step 400 is based on the Gram-Schmidt orthogonalization method referred as the orthogonal empirical mode decomposition OEMD. OEMD, which has mentioned, is described in G. D'Angelo: 'Advanced Signal Analysis Method to Evaluate the Laser Welding Quality', AKL—International Laser Technology Congress, May 9-11, 2012 in Aachen, operated as follows:

using EMD, signal x(t) (which in the method described correspond to denoised signal x̃(t), denoised by the noise removal method 200, is expressed as the sum of n IMF components $\overline{c}_j(t)$ (j=1, 2, ..., n), i.e. $IMF_1$ ... $IMF_n$, calculated at step 300 and the final residue $r_n(t)$, i.e. $x(t)=\sum_{j=1}^{n}\overline{c}_j(t)+r_n(t)$ first, $c_1(t)$ is defined as the first orthogonal IMF (OIMF) component, $OIMF_1$, of signal x(t), where $c_1(t)=\overline{c}_1(t)$ since it is not theoretically guaranteed that $\overline{c}_2(t)$ is orthogonal to $\overline{c}_1(t)$, therefore, in order to get the second OIMF component, $OIMF_2$, of x(t), one may adopt this measure which removes partial $c_1(t)$ from $\overline{c}_2(t)$. Then $c_2(t)$ is given by:

$$c_2(t)=\overline{c}_2(t)-\beta_{21}c_1(t)$$

where, $c_2(t)$ is the second OIMF component of x(t) which is orthogonal to $c_1(t)$, $\beta_{21}$ is defined as the orthogonality coefficient between $\overline{c}_2(t)$ and $c_1(t)$. Producing $c_1(t)$ and performing integral transform about time t of both sides of the last equation and using the orthogonal characteristic between $c_2(t)$ and $c_1(t)$, it can be shown that $\beta_{21}$ can be deduced as follow:

$$\int_0^T c_1(t)c_2(t)dt = \int_0^T \overline{c}_2(t)c_1(t)dt - \beta_{21}\int_0^T c_1^2 dt = 0$$

$$\beta_{21} = \int_0^T \overline{c}_2(t)c_1(t)dt \bigg/ \int_0^T c_1^2 dt$$

$$\beta_{21} = \{\overline{c}_2\}^T\{c_1\}/\{c_1\}^T\{c_1\} = \sum_{i=1}^{N}\overline{c}_{2i}c_{1i} \bigg/ \sum_{i=1}^{N} c_{1i}^2$$

adopting the same measure proposed above, by removing all the former j OIMF components from the (j+1)th IMF component of x(t) from EMD, it can be obtained the (j+1)th OIMF component of x(t), $c_{j+1}$ (j=2, ..., n−1) is given by $$c_{j+1}(t) = \overline{c}_{j+1}(t) - \sum_{i=1}^{j}\beta_{j+1,i}c_i(t)$$

producing $c_k(t)(k\leq j)$ and performing integral transform about time t of both sides of the last equation expressing $c_{j+1}(t)$ and using the orthogonal characteristic between $c_k(t)$ and $c_i(t)$ (i≠k), it can be shown that $\beta_{j+1,i}$ can be deduced as follow:

$$\int_0^T c_{j+1}(t)c_k(t)dt == \int_0^T \overline{c}_{j+1}(t)c_k(t)dt - \sum_{i=1}^{j}\beta_{j+1,i}\int_0^T c_k(t)c_i(t)dt = 0$$

$$\beta_{j+1,i} == \{\overline{c}_{j+1}\}^T\{c_i\}/\{c_i\}^T\{c_i\} = \sum_{m=1}^{N}\overline{c}_{j+1,m}c_{i,m} \bigg/ \sum_{i=1}^{N} c_{i,m}^2$$

The above orthogonal processing process for IMF components is referred as the orthogonal empirical mode decomposition (OEMD). After performing some algebraic operation, signal x(t) is expressed as:

$$x(t) = \sum_{j=1}^{n} a_j c_j(t) + r_n(t) \text{ where,}$$

$$a_j = \sum_{i=j}^{n} \beta_{i,j} (j = 1, 2, \ldots, n), \beta_{i,j} = 1 (i = j)$$

It should be noted that the OEMD method do not change the extraction process of IMF from EMD, which is performed at step 300. Furthermore, owing to the almost orthogonality existed among IMFs, the OEMD for extracting OIMF can not only basically guarantee the attribute of intrinsic\mode function, but also ensure the exact orthogonal among OIMFs.

Figure 7:
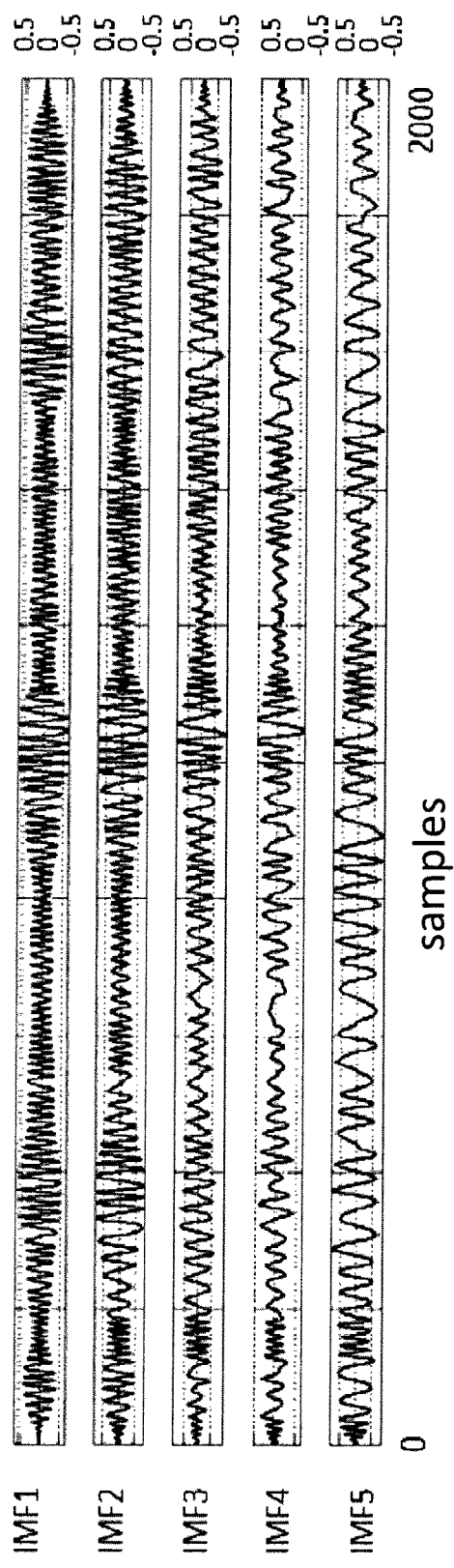
FIG. 7 is a diagram of an orthogonal intrinsic mode function.

FIG. 7 shows the Orthogonal Intrinsic Mode Functions, OIMF1 ... OIMF5, displaying the respective spectra. The OEMD procedures, as mentioned, works as a blind filters bank, without modelling the filter.

With reference to the operation of calculating 500 for each intrinsic orthogonalized component (OIMF1 ... OIMFn−1) the respective energy, and the following step 600-800 based on energy calculations, it is here preliminary introduced the Teager-Kaiser energy operator (TKEO).

The energy of a signal x(t), for instance corresponding to the denoised signal x̃(t), is given by the equation:

$$E = \int_{-T}^{T} |x(t)|^2 dt$$

This is not the instantaneous summed energy, but the energy of the signal over a time 2T. Another way to estimate a signal's energy, is to use the squared absolute value of the different frequency bands of the Fourier transformed signal as a measure of the energy levels of respective bands. The energy to generate a simple sinusoidal signal varies with both amplitude and frequency. Finally, in order to estimate the instantaneous energy of a signal is using an energy tracking operator. This is the so called Teager-Kaiser Energy Operator (TKEO), $\Psi[.]$, and is defined as:

$$\Psi_c[x(t)] = [\dot{x}(t)]^2 - x(t)\ddot{x}(t)$$

where x(t) is the signal and $\dot{x}(t)$ and $\ddot{x}(t)$ are its first and second derivatives respectively. In the discrete case, the time derivatives of the previous equation can be approximated by time differences:

$$\Psi[x(n)] = x_n^2 - x_{n+1}$$

The TKEO offers excellent time resolution because only three samples are required for the energy computation at each time instant.

Therefore as mentioned, in step 500 is calculated for each intrinsic orthogonalized component OIMF1 ... OIMFn−1 the respective energy.

Figure 8:
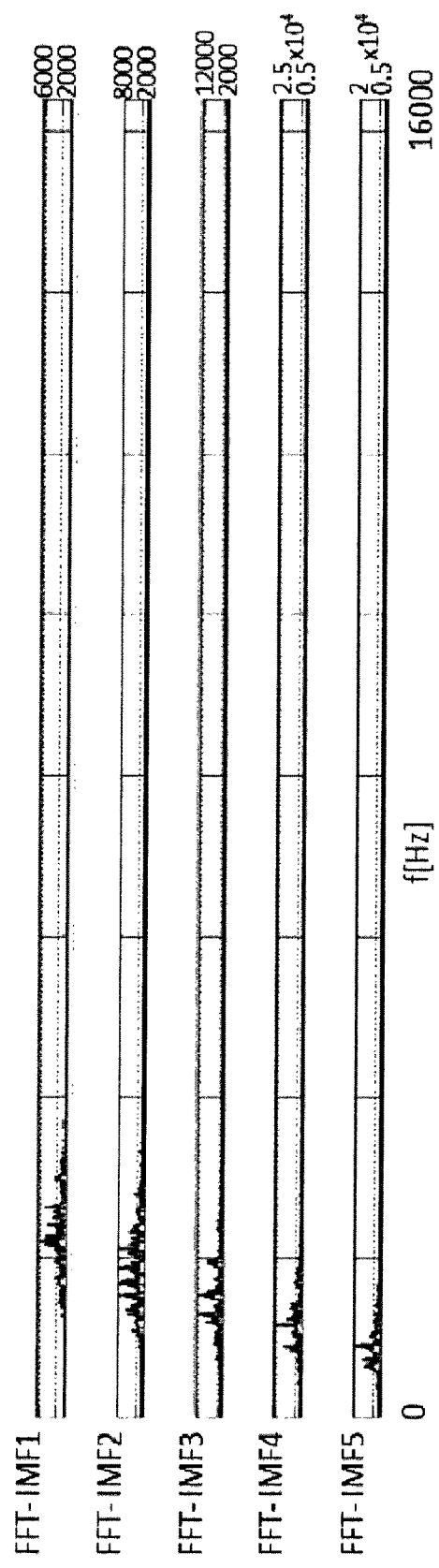
FIG. 8 is a diagram of a spectrum of orthogonalized components.
Figure 9:
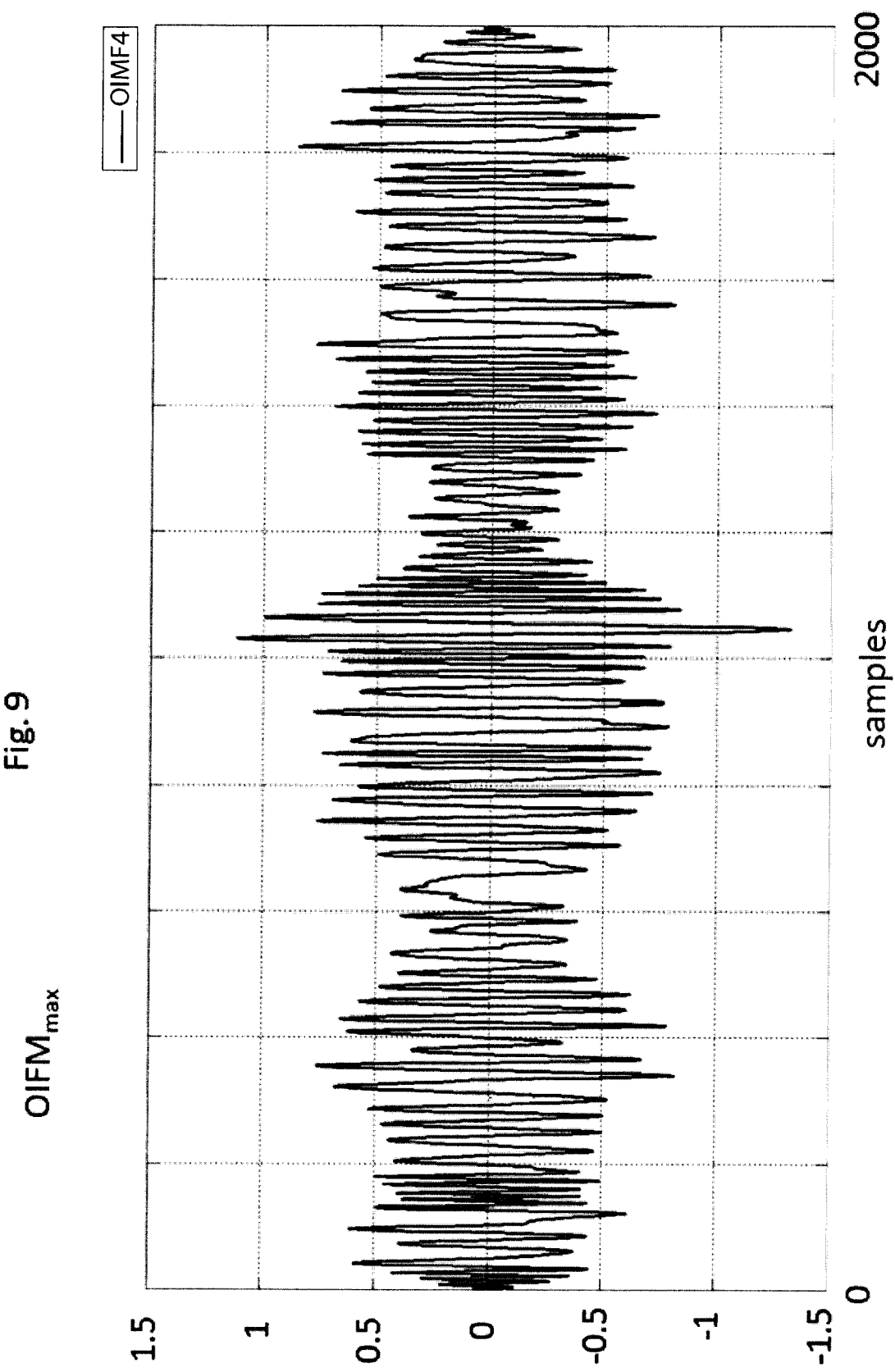
FIG. 9 is another diagram of the spectrum of orthogonalized components.

In step 600 is selected the intrinsic orthogonalized component with the highest energy value OIFMmax. With reference to the example of FIG. 7, for each intrinsic OIMF1 ... OIMF1 it is calculated the energy and selected the one with highest energy value: higher the energy value, higher the signal content. In FIG. 8 are shown the spectra of OIMF1 ... OIMF5 In the example, OIMF4 has the highest energy value, i.e. it is the orthogonalized component with the highest energy value OIFMmax and it is also shown in FIG. 9.

Figure 10A:
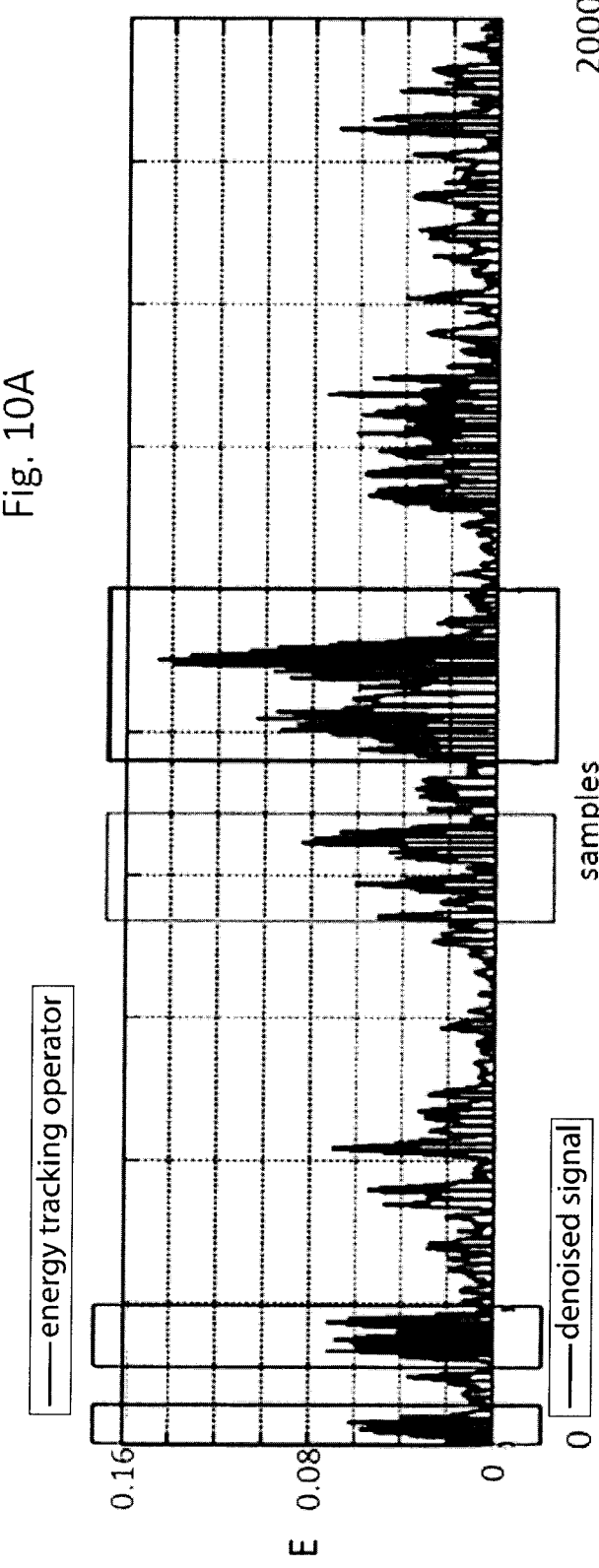
FIG. 10A is a diagram of the instant freeze energy of an energy signal of processed according to the method of FIG. 2.
Figure 10B:
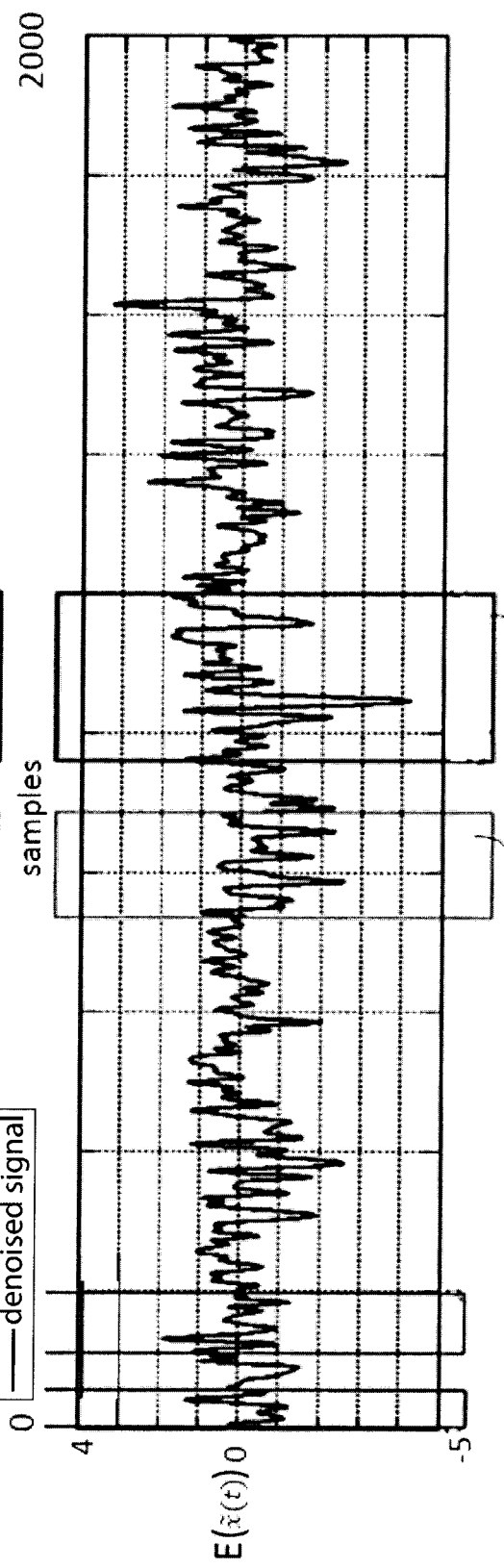
FIG. 10B is a diagram showing the energy of a denoised signal processed according to the method of FIG. 2.

Then is performed the operation of estimating 700 the instantaneous energy E of the intrinsic orthogonalized component with the highest energy value OIFMmax applying a energy tracking operator, i.e the TKEO operator. FIG. 10A shows the instantaneous energy of a energy signal E of the intrinsic orthogonalized component with the highest energy value OIFMmax without a conventional SSA and FIG. 10B shows the energy E(x̃(t)) of the denoised signal x̃(t).

On this signal E(x̃(t)) is performed according to operation 800 a procedure of defect identification on the instantaneous energy (E) of the intrinsic orthogonalized component with the highest energy value (OIFMmax).

The signal part contained within the box B1 can be considered as a severe instability (defect), the signal part contained within the box B2 can be considered as an acceptable instability (defect). The evaluation is performed on the basis of a threshold on the amplitude of instantaneous energy E.

Of course other known procedures can be used to perform the defect analysis procedure 800, such as the method described in EP-A-1767308 or in EP-A-1275464.

Thus, the modified SSA noise removal allows an optimal choice of window length and grouping strategy to obtain a good separation between trend and noise in the signal, i.e. avoiding that trend components become mixed with noise components in the reconstruction of the signal.

This is particularly effective in the monitoring of laser processes, where it is to be evaluated a signal acquired by a working process, having multiple frequency components. The monitoring method described, by decomposition in single components and analysis, allows to detect if the defects are present, using the TKEO operator to determine the the presence of defects occurred during the welding as well as to localize the defects.

The method therefore allows to determine in a quick way and without use of comparison to a reference signals, which signals generated by process are indicative of defects and can be analyzed in detail to determine the position and/or the type of defects.

Naturally, without altering the principle of the invention, the construction details and the embodiments may vary widely from what is described and illustrated purely by way of example herein, without thereby departing from the scope of the present invention.

The method is directed to laser welding process, but also to other working process, in particular involving laser, such as laser cutting processes. The method for performing a noise removal operation described can be used also to remove noise from electrocardiographic or electromyographic signal.

The sensor used to acquire the signal from the process can be any of the sensors used in the known techniques of quality monitoring of industrial working processes producing a non-stationary signal. By way of example, with reference to laser welding or cutting, the sensor can be a photodiode acquiring the radiation reflected by the spot on which the laser operates.

The invention claimed is:

1. A method for performing a noise removal operation on a signal acquired by a sensor obtaining a denoised signal, said noise removal operation including a Singular Spectrum Analysis,
said Singular Spectrum Analysis including performing iteratively:
an operation of decomposition of said acquired signal considered as one dimensional series, an operation of construction of a trajectory matrix, transforming said trajectory matrix in a form to which single value decomposition is applicable, an operation of single value decomposition on said transformed matrix computing eigenvalues and eigenvectors of said matrix, an operation of reconstruction of a one dimensional series corresponding to said denoised signal based on selected among said eigenvalues, wherein after the single value decomposition operation is provided, applying sequentially a single value decomposition starting from a given window value, in particular a value of three, for each iteration, calculating the root mean square value between the current and previous eigenvalue, calculating a minimum and its position of said root mean square value, and halting the iterations if said minimum is lower than a determined threshold value, otherwise increasing the window value and returning to the operation of decomposition of said acquired signal.

2. A method for monitoring the quality of an industrial working process, which includes identifying defects of the working process, of the type comprising the steps of:

acquiring a signal having multiple frequency components from the industrial working process, performing a noise removal operation on said acquired signal obtaining a denoised signal, decomposing said denoised signal y(t) in signals having single frequency components and performing a subsequent orthogonalization to obtain orthogonalized components having a single frequency component, calculating for each intrinsic orthogonalized component the respective energy, selecting the intrinsic orthogonalized component with the highest energy value, estimating the instantaneous energy of the intrinsic orthogonalized component with the highest energy value applying an energy tracking operator, performing a procedure of defect identification on the instantaneous energy of the intrinsic orthogonalized component with the highest energy value, and wherein said noise removal operation is performed according to the method of claim 1.

3. The monitoring method as claimed in claim 2, wherein said acquiring at least one signal having multiple frequency components from the industrial working process includes sensing a signal generated by the working process.

4. The monitoring method as claimed in claim 3, wherein said industrial process is a laser welding process or a laser cutting process.

5. The monitoring method as claimed in claim 3, wherein said sensing a signal comprises sensing a radiation by a photosensor.

6. A system for monitoring the quality of an industrial process, comprising:

sensor means for measuring one or more process parameters, and an electronic control and processing unit for processing the signals emitted by said sensor means, wherein:

said electronic control and processing unit is configured to process the signals emitted by said sensor means and to perform the method for monitoring the quality of an industrial process as claimed in claim 3.

7. A computer product directly loadable into the memory of an electronic computer and comprising software code portions to perform the method as claimed in claim 3, when the product is run on a computer.

8. The monitoring method as claimed in claim 2, wherein said industrial process is a laser welding process or a laser cutting process.

9. The monitoring method as claimed in claim 8, wherein said sensing a signal comprises sensing a radiation by a photosensor.

10. A system for monitoring the quality of an industrial process, comprising:

sensor means for measuring one or more process parameters, and an electronic control and processing unit for processing the signals emitted by said sensor means, wherein:

said electronic control and processing unit is configured to process the signals emitted by said sensor means and to perform the method for monitoring the quality of an industrial process as claimed in claim 8.

11. A computer product directly loadable into the memory of an electronic computer and comprising software code portions to perform the method as claimed in claim 8, when the product is run on a computer.

12. The monitoring method as claimed in claim 2, wherein said sensing a signal comprises sensing a radiation by a photosensor.

13. A system for monitoring the quality of an industrial process, comprising:

sensor means for measuring one or more process parameters, and an electronic control and processing unit for processing the signals emitted by said sensor means, wherein:

said electronic control and processing unit is configured to process the signals emitted by said sensor means and to perform the monitoring method as claimed in claim 12.

14. A computer product directly loadable into the memory of an electronic computer and comprising software code portions to perform the method as claimed in claim 12, when the product is run on a computer.

15. The method of claim 12 wherein said photosensor comprises a photodiode.

16. A system for monitoring the quality of an industrial process, comprising:

sensor means for measuring one or more process parameters, and an electronic control and processing unit for processing the signals emitted by said sensor means, wherein:

said electronic control and processing unit is configured to process the signals emitted by said sensor means and to perform the method for monitoring the quality of an industrial process as claimed in claim 2.

17. A computer product directly loadable into the memory of an electronic computer and comprising software code portions to perform the method as claimed in claim 2, when the product is run on a computer.

18. A noise removal method according to claim 1 wherein the method can be used also to remove noise from electrocardiographic or electromyographic signal.

19. A computer product directly loadable into the memory of an electronic computer and comprising software code portions to perform the method as claimed in claim 1, when the product is run on a computer.

20. The method of claim 1 wherein said determined threshold value is 1.

* * * * *